(12) United States Patent
Joyce et al.

(10) Patent No.: US 7,851,021 B2
(45) Date of Patent: Dec. 14, 2010

(54) TREATED WET PROCESS HARDBOARD

(75) Inventors: John M. Joyce, Millers Creek, NC (US); Clemente R. Diaz, Clemmons, NC (US); Simon Fitzgerald, N. Wilkesboro, NC (US)

(73) Assignee: Louisiana-Pacific Corporation, Nashville, TN (US)

( * ) Notice: Subject to any disclaimer, the term of this patent is extended or adjusted under 35 U.S.C. 154(b) by 1141 days.

(21) Appl. No.: 11/468,309

(22) Filed: Aug. 30, 2006

(65) Prior Publication Data

US 2008/0057137 A1    Mar. 6, 2008

(51) Int. Cl.
*B05D 7/06* (2006.01)
*B32B 21/02* (2006.01)

(52) U.S. Cl. ............... 427/297; 162/128; 428/292.4

(58) Field of Classification Search .............. 427/294
See application file for complete search history.

(56) References Cited

U.S. PATENT DOCUMENTS

| | | | |
|---|---|---|---|
| 2,194,827 A | 3/1940 | Gordon | 134/78.6 |
| 4,038,131 A * | 7/1977 | Baldwin et al. | 162/103 |
| 4,871,473 A | 10/1989 | Goettsche et al. | 252/400.52 |
| 4,879,083 A | 11/1989 | Knudson et al. | 264/122 |
| 5,478,598 A | 12/1995 | Shiozawa | 427/297 |
| 5,972,266 A | 10/1999 | Fookes et al. | 264/122 |
| 6,030,562 A | 2/2000 | Lehtinen et al. | 264/83 |
| 6,521,288 B2 | 2/2003 | Laks et al. | 427/180 |
| 6,881,247 B2 | 4/2005 | Batdorf | 106/15.05 |
| 2001/0037035 A1 * | 11/2001 | Kutcel | 558/286 |

* cited by examiner

*Primary Examiner*—Timothy H Meeks
*Assistant Examiner*—Collette Ripple
(74) *Attorney, Agent, or Firm*—Waddey & Patterson, P.C.; James R. Cartiglia

(57) ABSTRACT

A method of delivering and retaining zinc borate within a wet process hardboard is disclosed wherein process parameters are controlled and the borate is included in the overlay slush process of wet board processing.

20 Claims, 7 Drawing Sheets

Cross-Section
of Treated Hardboard

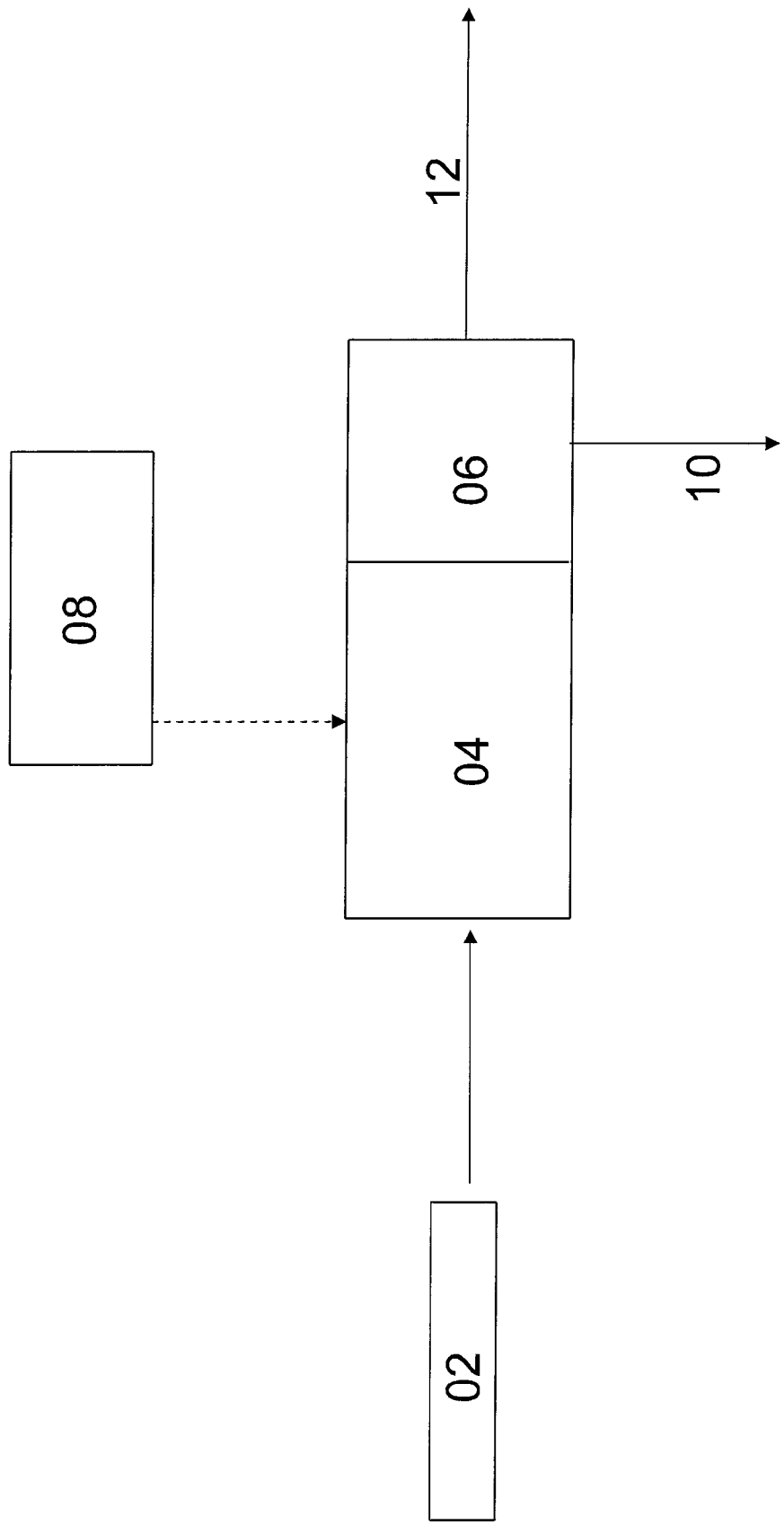
Figure 1 Simplified Flow Diagram

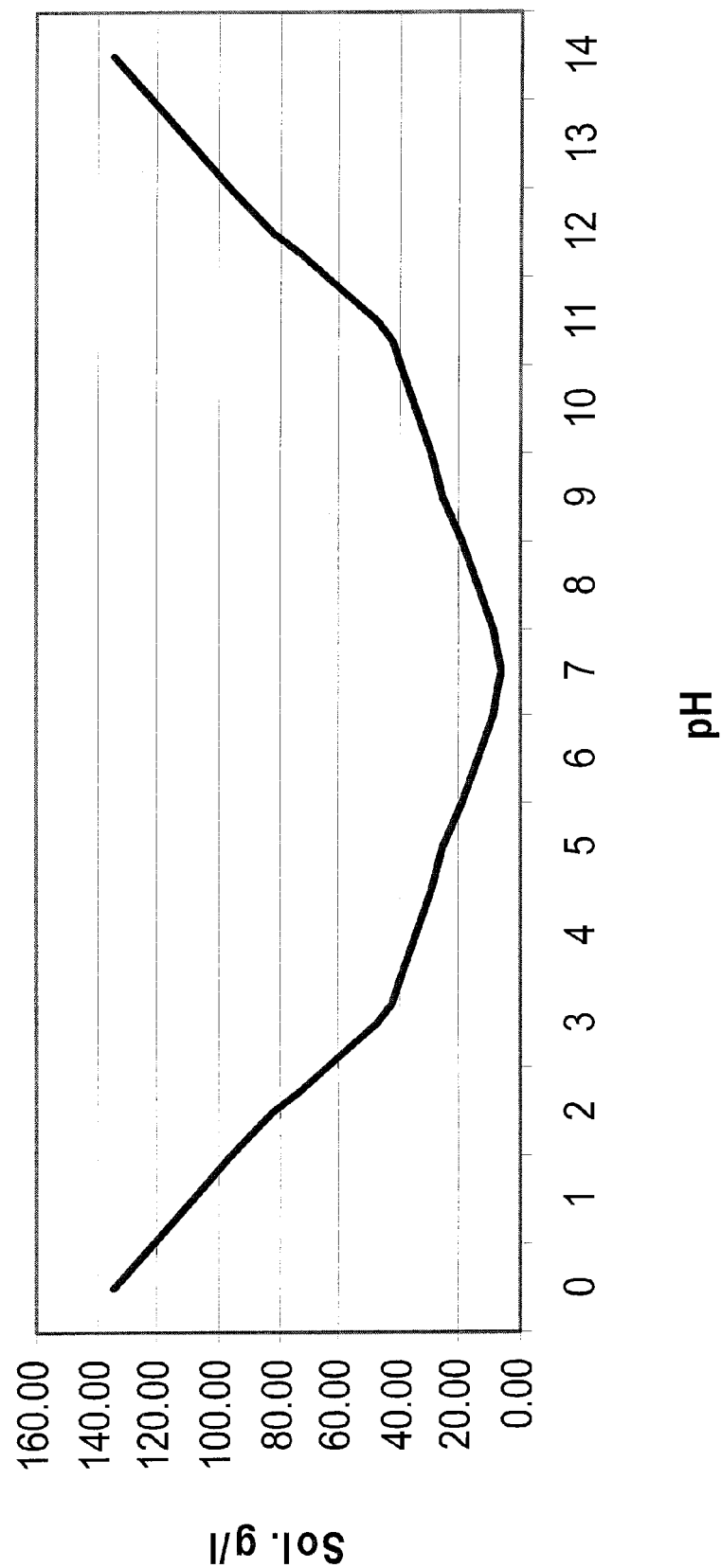

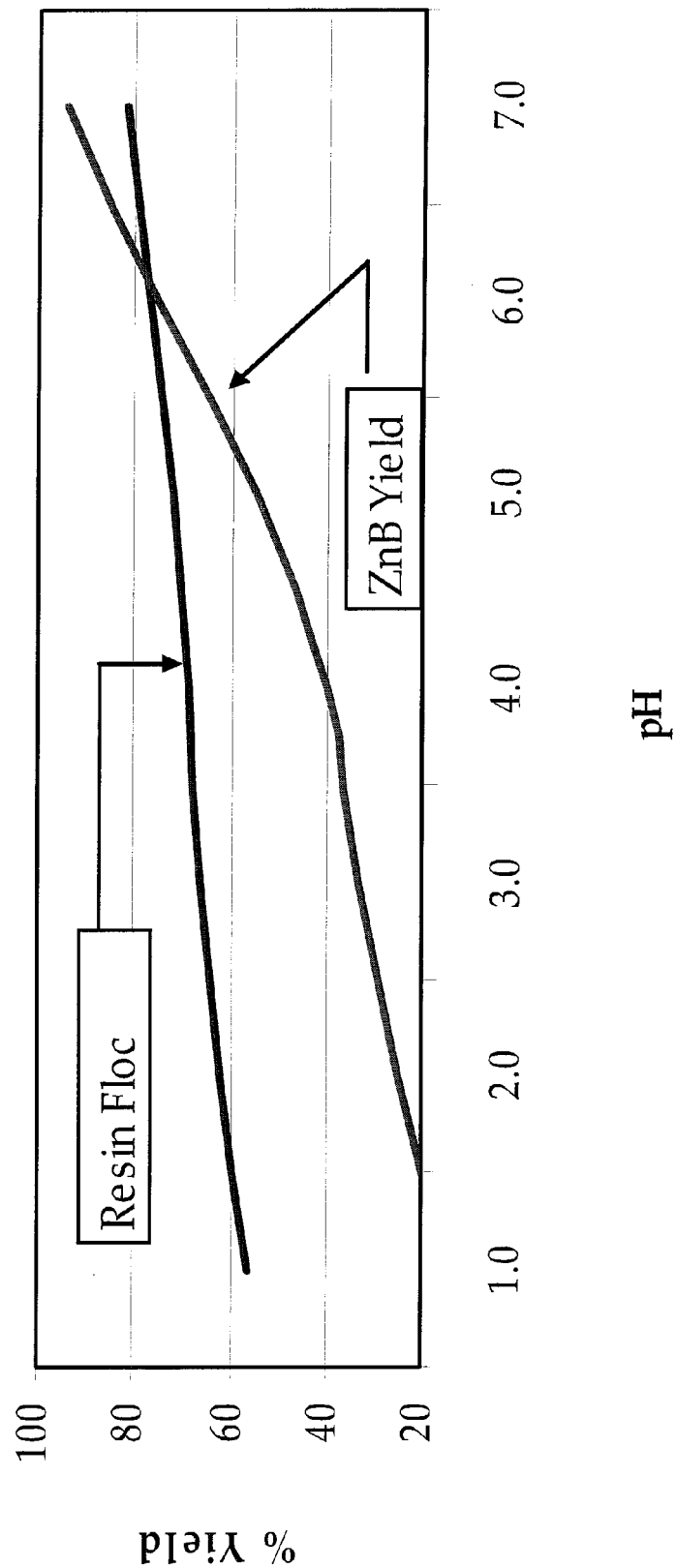
Figure 3 - Resin/ZB Floc Yield vs. pH

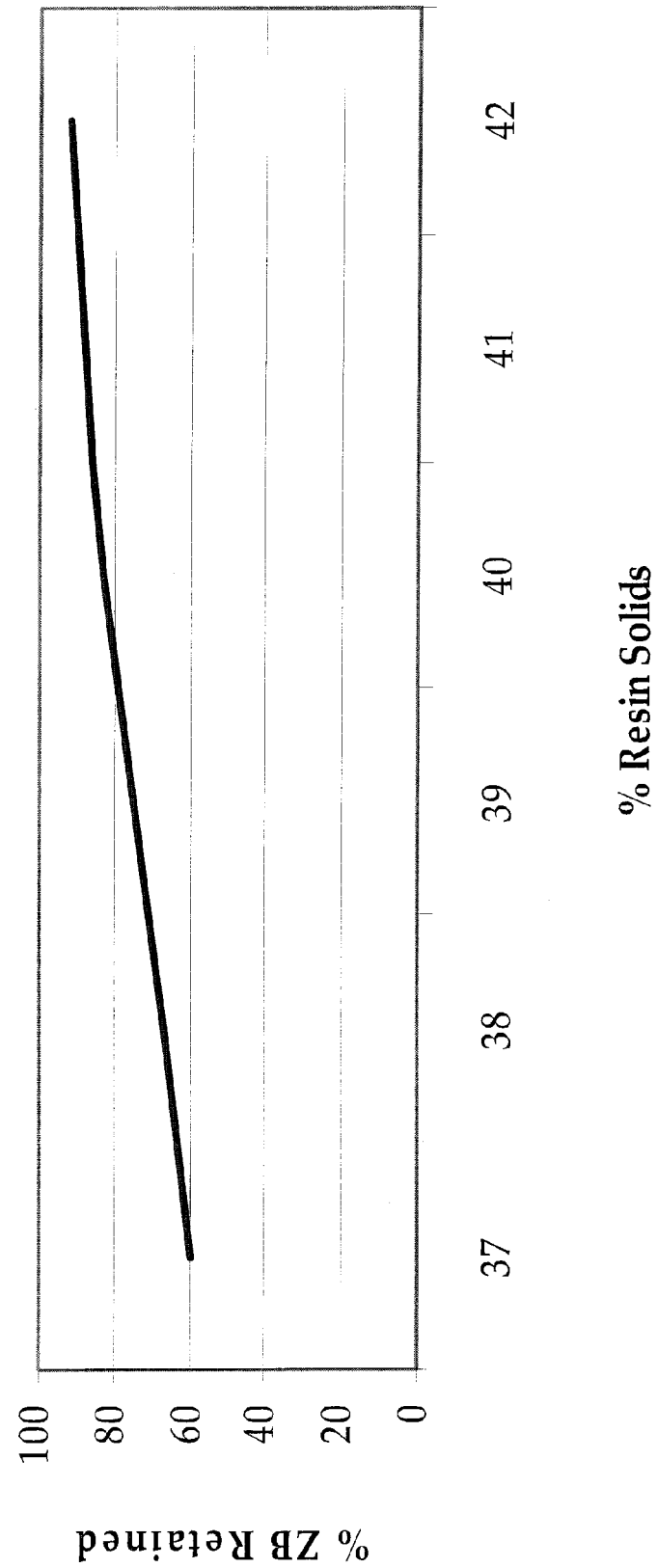

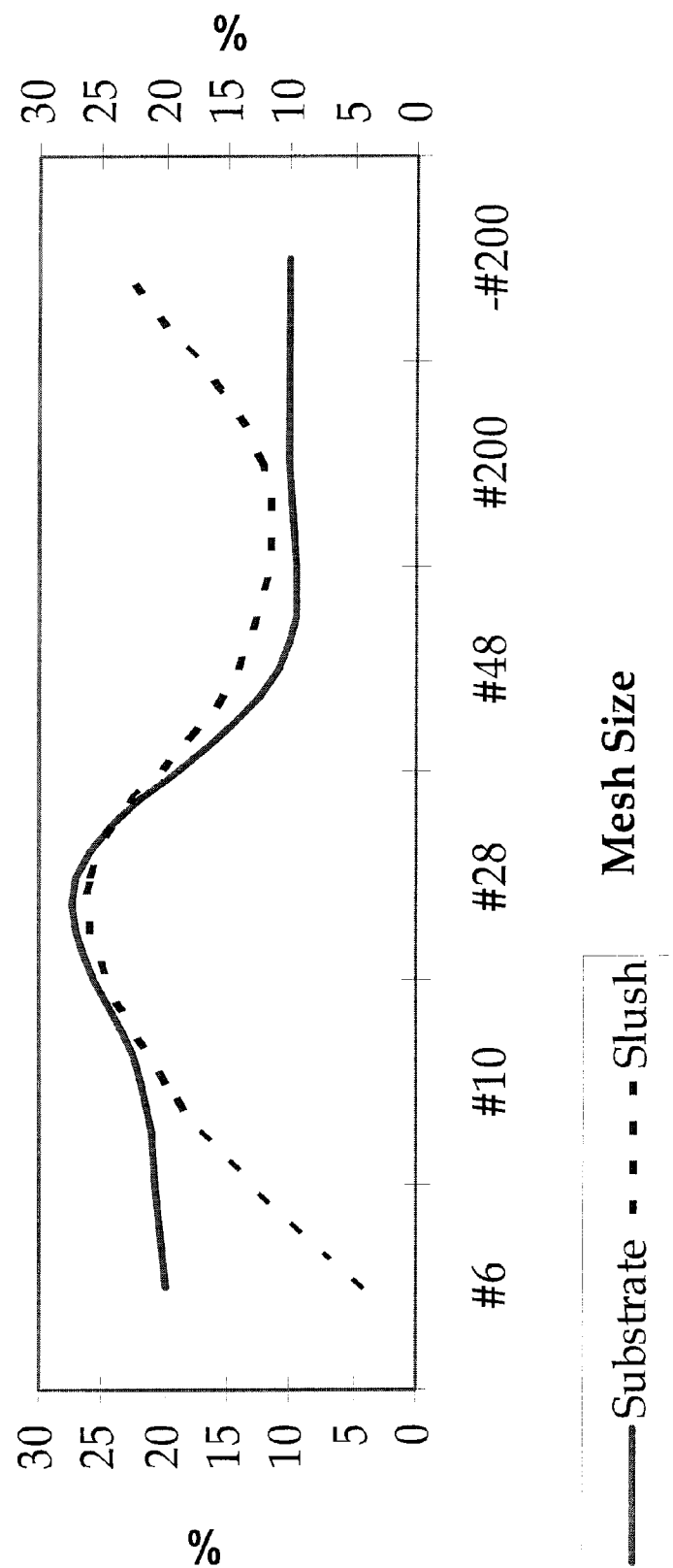

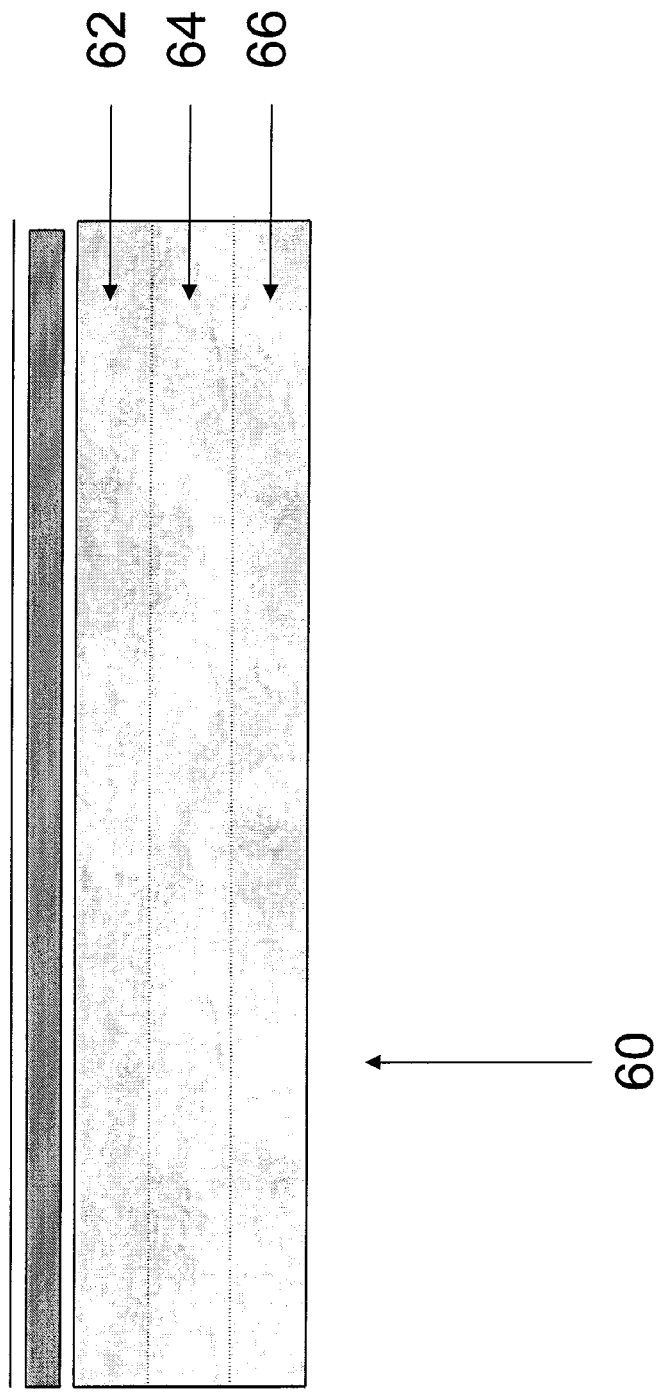
Figure 6 Cross-Section of Treated Hardboard

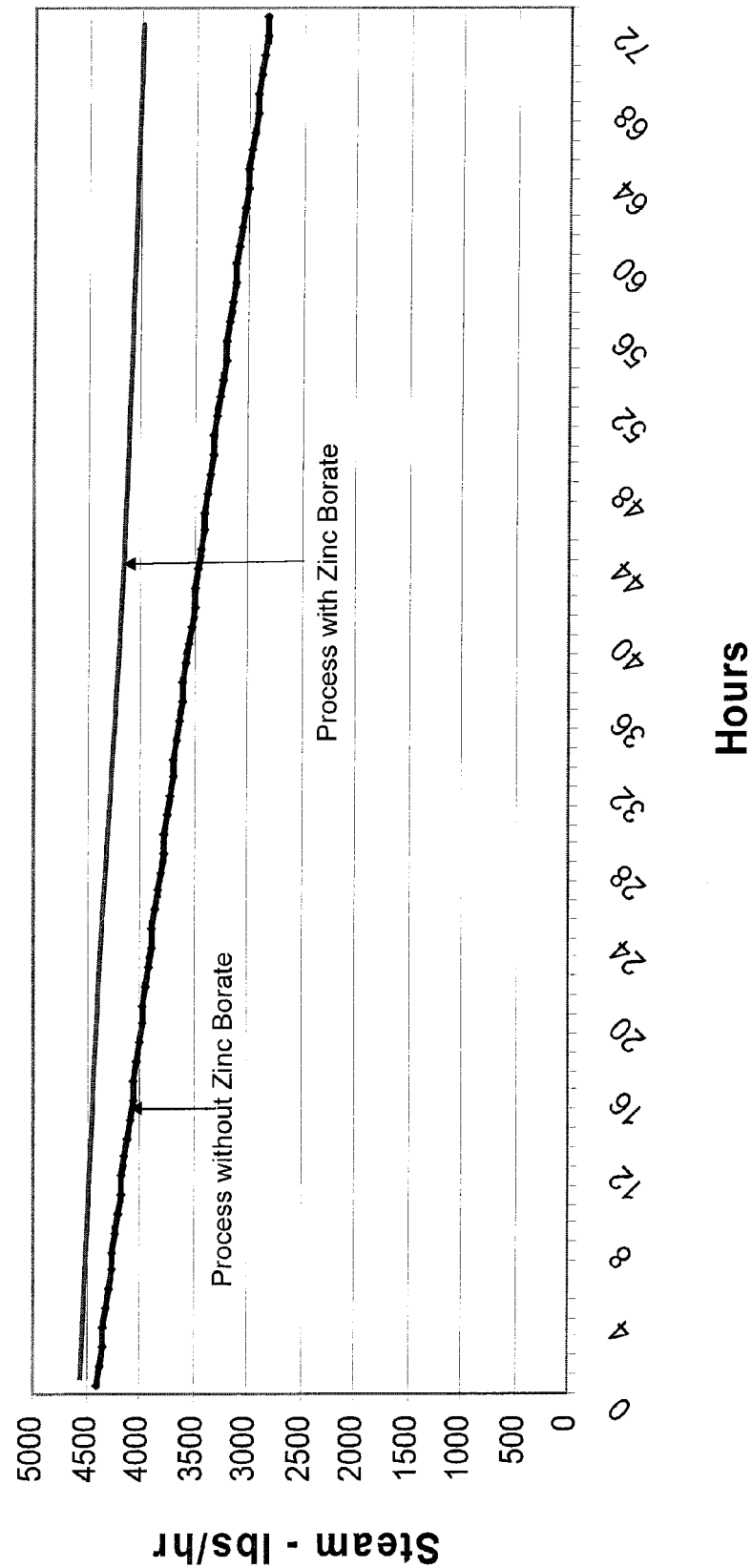

TREATED WET PROCESS HARDBOARD

BACKGROUND OF THE INVENTION

1. Technical Field

The present invention relates to a method of delivering and retaining borate in a wet process hardboard substrate useful for construction applications such as residential and commercial wood-frame construction. More particularly, the present invention relates to a method of impregnating a wet process hardboard with zinc borate to create a product resistant to long-term decay caused by the penetration or infiltration of water and fungus as well as damage caused by termites and other insects. The invention also includes the hardboard containing zinc borate produced by the novel process.

2. Background Art

Zinc borate is a known and established wood preservative for enhancing the resistance of wood and wood composite compounds against natural environmental stresses. Zinc borate has a nominal chemical formula of $2ZnO-3B_2O_3-3.5H_2O$ and a median particle size of 7 microns. Borates are generally non-toxic to humans, mammals, and most aquatics at low to moderate concentration levels, but they do impede the metabolism of soil or wood-borne organisms such as fungi, mold, and some bacteria. Additionally, borates have been proven to be toxic to many insects, most notably termites. Thus, borates have experienced long use in the wood manufacturing process dating from the mid-1900's as one of the very first wood preservatives.

Borates can be introduced to wood as either boric acid or as sodium borate, calcium borate, or zinc borate. The borate ion itself imparts the predominant fungal, rot, and insect resistant qualities to the wood substrate. However, because the borate ion is highly soluble, it requires a generally inert and stabilizing chemical carrier to which it can bond and become electrochemically neutral. To achieve this electrochemical neutrality and thus render the borate ion virtually insoluble, borates are often reacted with sodium, calcium, or zinc (e.g. cations with a valence charge of +2). Sodium borate has been the most common borate compound used for wood preserving. However, zinc borate has gained popularity and today is becoming one of the more popular wood preservatives due to the zinc portion of the zinc borate chemistry having some level of water, fungal, and insect-resistant properties. As a result, the exterior wood manufacturing and/or wood composite industry has recognized zinc borate as one of the best overall wood preserving compounds.

Traditionally, the use of borate compounds as wood preservatives has been exclusively for treated lumber or I-joist manufacturing and dry process wood composite manufacturing such as Oriented Strand Board (OSB) or Medium Density Fiberboard (MDF). In the case of treated lumber or I-joists, sodium borate is typically used and is applied via a direct aqueous spray process. In the case of the dry processing of wood composites in board mills such as OSB or MDF, zinc borate is introduced to the process at a blending operation. Physically, zinc borate is a stable, white, high molecular weight, crystalline powder that when mixed with water, generally does not dissolve. Zinc borate is initially formulated from zinc oxide, boric acid, and water. Furthermore, even in the presence of water at a neutral pH, the zinc borate does not typically dissociate or experience phase or chemical change. However, if the pH of the zinc borate and dry wood article were to become considerably acidic or alkaline, for instance experience a pH of 3.0 or lower, or conversely 9.0 or higher, the zinc borate would become progressively more soluble and begin to chemically change to zinc hydroxide (or oxide) and boric acid. This dissolved product of zinc and boric acid would no longer possess the favorable properties of zinc borate and therefore have a substantially reduced value as a wood preservative.

Zinc borate can and has been used with great success in dry process wood composite board mills where the wood's interior moisture content is considerably low (e.g. typically <10%) because the borate can bond to the phenol formaldehyde (PF) or methyl diphenyl isocyanate (MDI) resins through both physical and chemical bonding. Conversely, in wet process, composite wood manufacturing environment such as hardboard, specifically exterior hardboard siding, the ability to introduce and retain borate compounds has been met with virtually no success. Because borates can be highly soluble in water, the borates would simply convert to dilute boric acid solutions and be lost during the traditionally low pH and high temperature wet forming and/or wet-pressing processes.

Much research has been conducted on creating different types of preservatives as well as methods of making preserved dry board. For example, U.S. Pat. No. 4,871,473 by Goettsche et al., discloses a wood preservative based upon a zinc compound in aliphatic carboxylic acid which also contains a polyamine for creating a preservative for wood which does not cause discoloration. Furthermore, this disclosed compound is stable and the solution does not precipitate and can be applied by spraying, dipping, or impregnating the wood, or also by painting it upon the wood.

In Knudson et al. (U.S. Pat. No. 4,879,083), a method is disclosed for making particle board impregnated with a borate compound. Specifically, the method includes treating the wood particles with phenol formaldehyde resin and adding either anhydrous borax or zinc borate compound and then consolidating the treated particles under heat and pressure under normal processing conditions.

In Shiozawa, U.S. Pat. No. 5,478,598, a wood preservative and method for treating a wood is disclosed wherein the wood preservative compound contains a copper compound, a zinc compound, an aqueous salt, and a volatile basic compound. The wood preservative is alleged to be fungi resistant, insect resistant, fixed into the wood and also allegedly possesses a low toxicity.

In U.S. Pat. No. 5,972,266, Fookes et al. discloses a process for making a consolidated wood board containing zinc borate. This processes discloses first forming a sprayable aqueous emulsion of zinc borate and applying the emulsion to the wood strands prior to consolidating the wood strands together to form the composite wood material.

In Lehtinen et al. (U.S. Pat. No. 6,030,562), a method of forming a consolidated wood article is disclosed wherein zinc borate and a resin are mixed with either wood chips or wood fibers to form a wood board. The process further includes pressing the combination of zinc borate resin with the substrate material under heat supplied by steam to provide the wood composite article.

Laks et al. (U.S. Pat. No. 6,521,288) describes production of a wood product by incorporating a nanoparticle containing a biocide with wood particles and applying a sufficient pressure to the wood particles to form the wood product. It is suggested that this disclosed process is more desirable and less toxic than other methods.

In U.S. Pat. No. 6,881,247, Batdorf discloses a protective barrier coating for use upon wood. The disclosed coating includes a metal borate compound, a zinc compound, magnesium hydroxide, and a water-based binder for protection against insects, mold or mildew, and fire or water damage.

Despite the success of incorporating zinc borate into wood or wood composites during dry processing, zinc borate has been extremely ineffective in wood preservation of wood articles produced through wet processing. The zinc borate typically will be made soluble within the wet process wood article and thus will not impart the resistant characteristics to a hardboard produced through wet processing.

What is desired, therefore, is a method for effectively retaining borate in a wet process hardboard product, such as an exterior siding product, wherein the borate containing wet process hardboard meets or exceeds the minimum standards for wood composites set forth by the American Wood Preservers' Association, specifically 0.38% BAE for decay caused by basidiomycetes and 0.30% BAE for subterranean termite/insect resistance. The net result would be the manufacture of a product which is largely resistant to termitic degradation and fungal rot.

BRIEF SUMMARY OF THE INVENTION

The present invention provides a method which is uniquely capable of delivering and retaining zinc borate in a wet process, wood composite, hardboard substrate, such as an exterior substrate. The inventive process is able to create a hardboard article exhibiting long-lasting fungal, decay, and termite resistance not heretofore seen. In addition, the novel process allows for the zinc borate to be maintained within the hardboard for an extended duration of time without a significant fraction of the zinc borate leaching from the hardboard substrate. Furthermore, the novel method allows for zinc borate to be incorporated in the hardboard throughout the normal wet processing allowing the hardboard to be sized, machined, or otherwise finished for the desired application.

More particularly, the inventive process uses an existing slush overlay process and through an alteration of the process chemistry, sufficient quantities of zinc borate can be maintained in wet process hardboard.

An important characteristic for any exterior wood composite and specifically for the exterior wet process hardboard substrate in question is the weight percentage of zinc borate within the wood article. For such applications, the American Wood Preservers' Association has established a general standard for decay and fungal resistance in which zinc borate must be present in a wood composite substrate at levels equal to or exceeding 0.38% BAE. Similarly, the AWPA minimum general standard for termite resistance in a zinc borate containing wood composite substrate is 0.30% BAE. The inventive process allows for zinc borate to be present in an exterior, wet process, hardboard siding product well in excess of the minimum standards set forth by the AWPA.

The inventive process incorporates zinc borate into the slush overlay section of the wet hardboard process to provide the zinc borate to the hardboard substrate. In addition, the pH of the zinc borate solution, the slush, and also the hardboard substrate should be controlled, by which is meant that the zinc borate solution, overlay slush, and the hardboard mat have either a base or acid added to their respective components so that their respective pH is maintained at its specific level. Optimally, the pH of the inventive process is higher than the pH of the prior art thus allowing for the zinc borate and slush to be more readily received and held by the hardboard substrate.

The hardboard substrate should have a pH controlled in the range of from about 2.0 to about 6.0, more preferably in the range from about 4.0 to about 5.0. Additionally, the pH of the overlay slush should be of from about 4.0 to about 10.0 and more preferably from about 7.0 to about 8.0.

Advantageously, the temperature should be controlled during the wet processing for adequate retention of the zinc borate in the wet process hardboard substrate. While the temperature of the existing hardboard mat substrate should have a target range of from about 43° C. to about 60° C., and more preferably of from about 48° C. to about 55° C. to help preclude deleterious impacts to the process and product, the overlay slush temperature should be reduced and controlled to approximately 15° C. to about 33° C. and more preferably of from about 21° C. to about 24° C. Notably, the solubility of the zinc borate within the overlay slush changes very favorably when the temperature of the overlay slush is decreased from the prior range of about 48° C. to the inventive and preferable target temperature range of from about 21° C. to about 24° C.

Advantageously, to reduce process waste, hardboard substrate dust created from the cutting, sawing, finishing, and final processing of the zinc borate fixed hardboard substrate is collected and recycled back for the integration into the main hardboard mat and overlay slush allowing for both a significant cost savings and also to reduce environmental harm.

An object of the invention therefore is a process for creating a wet process hardboard siding in which zinc borate is both delivered and retained within the hardboard which can be used for exterior siding.

Another object of the invention is a process in which a wet process hardboard siding is created which is both decay and termite resistant.

Still another object of the invention is a method for creating a wet process hardboard siding having retained zinc borate throughout its structure to provide resistance against natural environmental stresses when used for building materials.

Yet another object of the invention is a method for producing wet process hardboard siding with zinc borate in which the pH is steadily controlled to a desired level throughout the process of creating the hardboard.

Another object of the invention is the actual wet process hardboard substrate containing zinc borate, which can be produced in a variety of siding sizes and configurations and which can be readily finished or processed to provide a product tailored for a consumer's desires.

These aspects and others that will become apparent upon review of the following description and can be accomplished by providing a process of creating a wet process hardboard siding in an overlay slush process having a controlled pH so that zinc borate is in a favorable condition to be delivered and retained within the wet process hardboard. The inventive process should maintain the pH of the overlay slush of from about 4.0 to about 10.0 and more preferably of from about 7.0 to about 8.0, and a pH of the main hardboard substrate of from about 2.0 to about 6.0, and more preferably of from about 4.0 to about 5.0. The total zinc borate content within the wet process hardboard article is up to about 1.5%, more preferably of from about 0.38% to about 1.5%, with a final hardboard density of from about 45 lb/ft$^3$ to about 55 lb/ft$^3$.

The inventive process advantageously has a overay slush process temperature of from about 15° C. to about 15° C. and more preferably of from about 21° C. to about 24° C. for optimum retention and delivery of the zinc borate into the wet process hardboard.

The inventive hardboard substrate can be subsequently finished to create a finished hardboard substrate containing zinc borate to the exact specifications of the consumer most typically for use as exterior siding. Furthermore, the processing dust which results from the cutting, sawing, and general finishing of the zinc borate containing hardboard substrate may be recycled back to the initial wet formation of the hardboard and overlay slush used for the impregnating of the hardboard.

It is to be understood that both the foregoing general description and the following detailed description provide embodiments of the invention and are intended to provide an overview of framework of understanding to nature and character of the invention as it is claimed.

BRIEF DESCRIPTION OF THE DRAWINGS

FIG. 1 is a simplified flow diagram of the slush overlay process.

FIG. 2 is a graph of the solubility of zinc borate as a function of pH.

FIG. 3 is a graph of the resin floe yield and zinc borate retention as a function of pH.

FIG. 4 is a graph of zinc borate retention as a function of resin solids.

FIG. 5 is a graph of zinc borate retention as a function of course fiber.

Fig. 6 is a cross-view illustration of the zinc borate gradient in wet process hardboard.

FIG. 7 is a graph illustrating press steam flow as a function of time for both a process using zinc borate and a process not using zinc borate.

DETAILED DESCRIPTION OF THE PREFERRED EMBODIMENTS

Wet process hardboard containing borate produced in accord with the present invention is prepared from an initial hardboard substrate and borate under process chemistry allowing for the borate to be delivered and retained within the wet process hardboard. Borates were originally discovered as quartz-like crystals in the 1870's. Essentially, borate is a hydrated salt compound derived from boron. Elemental, boron is rarely found by itself. Instead, boron reacts quickly with water and oxygen, usually to either produce boric acid or boron salt such as sodium metaborate or sodium tetroborate. Borates are generally non-toxic to humans, mammals, and most aquatics in low to moderate concentrations, but are proven to impede the metabolism of wood-born organisms, fungi (basidiomycetes specifically), mold, and some bacterias. Additionally, borates have also been proven to be toxic to numerous insect pests, most notably termites. Chemically, the borate ion itself imparts the predominant fungal rot and insect resistant qualities to a wood substrate. However, because the borate ion is highly soluble, the borate requires an electro-chemical carrier and stabilizer for delivery into the wood substrate and retention within the wood substrate. Suitable chemical carriers include sodium, calcium, and also zinc. Throughout wood preservation history, sodium borate has been by far the most common borate compound used in preserving wood materials. However, zinc borate has gained favorable interest more recently as zinc itself has some level of water, fungal, and insect-resistant properties. Most important however with respect to zinc borate in a wet process hardboard manufacturing environment is the fact that zinc is generally less soluble than either sodium or calcium and therefore at least modestly reduces the hydrolysis effect of water on the zinc borate compound.

The wet process hardboard substrate containing zinc borate is prepared by adjusting the system process parameters to retain the zinc borate. One consideration is the location of introducing zinc borate during the process of forming the wet process hardboard. Additionally, the process is tailored to preclude hydrolysis reaction of zinc borate by controlling the process pH and process temperature. Other chemical considerations include the interrelationship of zinc borate to the phenol formaldehyde resin present in the overlay slush as well as other solids and chemical agents present in the slush. Finally, the degree of delivery and retention of the zinc borate within the wet process hardboard is a function of the relationship of zinc borate to the fiber quality, fiber size, and wood speciation present throughout the process.

Zinc borate is introduced to the hardboard substrate during the slush overlay process. The slush overlay process can be characterized as a stand-alone process within the complete wet board processing in which a slush containing very finely refined wood fiber is deposited on the top surface of the primary wet substrate. The purpose of the slush overlay is to give the top surface of the boards superior embossing, durability, and paintability characteristics. As shown in FIG. 1, a simplified flow diagram of the overlay slush process portion of the wet process, hardboard substrate 02 is added to forming machine 04 containing vacuum section 06. Machine chest 08 contains the overlay slush which is fed to the forming machine 04 for overlying on the surface of hardboard substrate 02. The vacuum pressure from vacuum section 06 is applied to wet process hardboard substrate 02 once overlay slush from machine chest 08 is deposited on the top surface of wet process hardboard substrate 02. The pressure from vacuum section 06 is sufficient to pull the overlay slush down through wet process hardboard substrate 02. The excess overlay slush exits via route 10 and the treated hardboard substrate exits the slush overlay process via route 12 for subsequent processing.

By combining borate, preferably zinc borate, in the overlay slush contained in machine chest 08, the zinc borate is effectively delivered to hardboard substrate 02. By adjusting the process chemistry of the overlay slush process so that the overlay slush contains zinc borate, the zinc borate retention within the hardboard article can be well over the level of 1.0% BAE.

Zinc borate is generally a stable and electrochemically neutral compound even when in water as long as the pH of the water is neutral. When considering the ions separately, the zinc ion is highly insoluble in water and virtually unaffected by nominal changes in the pH, and thus, is easily retainable within a hardboard material. Conversely, the borate ion becomes increasingly more soluble in water as the pH changes from a neutral pH of 7.0. As such, even a nominal change in pH to a pH of 6.0 or 8.0 will cause some albeit small but determinate amount of the borate ion to quickly disassociate from the zinc ion to form boric acid. Furthermore, the more the pH changes from neutral, the more dramatic is the change in borate solubility within the solution. As illustrated by FIG. 2, as the process pH decreases toward a low of about 2.0, the rate of solubility of the borate increases to a level between about 80% and 90%. Practically, at this pH, most of the borate would be converted to boric acid when exposed to water and thus would not be retained within the hardboard substrate. When the pH is closer to neutral, 7.0, the borate ion is far less soluble and tends to remain more closely bonded to the zinc ion. With the zinc ion itself being high insoluble in water, the borate ion is also insoluble as it is attached to the zinc ion and will remain within the hardboard substrate. Specifically, the inventive process utilizes a pH of the substrate hardboard of from about 2.0 to about 6.0, more preferably in the range of from about 4.0 to about 5.0, and most preferably with a pH of the hardboard substrate at about 4.5. Furthermore, the pH of the overlay slush containing the zinc borate is of from about 4.0 to about 10.0, and more preferably of from about 7.0 to about 8.0. By elevating the process pH, a reduction in the rate of hydrolysis occurs and ensures that the chemical reaction and desired bonding between zinc and borate happen as desired.

Another component of the main hardboard mat and overlay slush is the resin constituent. Preferably, phenol formaldehyde resin is used as the resin constituent of both the main hardboard substrate and overlay slush and varies between 1% to 2% of the dry weight of the treated hardboard. In particular, solids of phenol formaldehyde resin are an important characteristic of the hardboard substrate and overlay slush as the wet process hardboard physical properties (e.g. strength, density, durability) improve with an increasing amount of retained resin solids. Specifically, the more resin solids that are flocculated in the hardboard wet chemistry process, the more resin solids that can be introduced and ultimately retained into the wet process hardboard. One method of increasing the total quantity or mass of resin flocs is by increasing the process pH of the wet process hardboard processing system. An increase in pH of the system process reduces the solubility of the phenol formaldehyde resin allowing for more solids to be retained within the board instead of exiting in the waste water from both the main substrate and slush overlay process system. The importance of retaining resin flocs within the wet process hardboard substrate is that the retention of zinc borate within the wet process hardboard substrate is also partially a function of the retention of the resin flocs within the wet process hardboard substrate. Otherwise stated, the greater the number of resin flocs produced and retained, the greater the zinc borate retention within the wet process hardboard substrate. A slight electrochemical bond occurs between the phenol formaldehyde resin and the zinc borate resulting in more bonding sites available for the zinc borate to attach with the increasing flocculation of the phenol formaldehyde resin.

As the flocculation yield of the resin increases, the physical properties of the board improve in both strength characteristics and zinc borate retention. With regard to the relationship between resin solids and zinc borate retention, with increasing pH, FIG. 3 represents the increase in both resin floc yield and zinc borate yield as the pH approaches neutral. Furthermore, as illustrated in FIG. 4, a 5 percentage point increase in resin solids, for example, from 37% to 42%, causes a 15% improvement in zinc borate retention within the wet process hardboard. Thus, as process pH favorably drives both the resin flocculation and zinc borate retention within the hardboard substrate, an optimum pH of both the hardboard and overlay slush system processes can be reached.

The ideal temperature for the slush overlay is in the range of from about 15° C. to about 33° C., and more preferably of from about 21° C. to about 24° C. while the temperature of the main hardboard process is in the range of from about 43° C. to about 60° C. and more preferably of from about 48° C. to about 55° C. While these two separate temperature ranges are quite divergent, they are both necessary for the respective zinc borate and resin chemistry performance. Zinc borate solubility is lowest when the temperature of the zinc borate solution and overlay slush is low. Correspondingly, resin flocculation and resin performance appears best when process temperature is high. However, the increased resin flocs produced and distributed at higher process temperatures in the main hardboard mat, give rise to many more electrochemical bonding sites for the zinc borate solids that are produced during the slush overlay process at lower temperatures.

An additional element of the overlay slush is wood fiber that makes up approximately about 3% of the total weight of the hardboard mat. A process parameter of the wood fiber in the overlay slush is the distinct fiber size of the wood fiber. Assuming the other process parameters of the system for creating the wet process hardboard are optimized, including the process pH, resin solids, and process temperature, a clear correlation exists between the percentage of fine fiber and a percentage of zinc borate retained within the hardboard substrate. Fiber used in the slush overlay process is mechanically refined 3 distinct times through primary, secondary, and overlay disc refining processes. Conversely, the fiber in the main hardboard mat is only refined 2 times and therefore more coarse than the overlay fiber. A Number 6 mesh screen is used to measure the amount of course fiber that is allowed into the overlay slush and subsequently used in making the wet process hardboard. In accordance with Tyler mesh size nomenclature, a Number 6 mesh screen allows particles through that measure less than 3,360 microns. Specifically, for use in the slush overlay process, a Number 6 mesh screen is used as a measure of the amount of coarse fiber passing through the prescribed screen opening. For example, a system process operating a Number 6 mesh specification between a low of 10% and a high of 20% would translate to between about 10% to about 20% of the fiber of the slush being coarse. Pertinent to the slush overlay process, this parameter of using a Number 6 mesh screen correlates to the speed at which water drains from the overlay on the top surface of the hardboard substrate in the forming of the treated hardboard. The main wet hardboard mat formation system processes cannot sustain high-speed production rates with very low percentages of coarse fiber as the drainage off the hardboard substrate would be too low (measured as "freeness" or "Williams Slowness"). However, as FIG. 5 illustrates, as the percentage of coarse fiber increases as defined by the percentage of fiber which cannot pass through the Number 6 mesh screen, the amount of zinc borate retained within the wet process hardboard decreases. Appropriately and conversely, the zinc borate retention within the hardboard substrate improves notably when finer fiber is produced (e.g. less fiber through the #6 mesh screen). Finer fiber has more effective surface area and is more tightly compacted when deposited upon the wet process hardboard substrate. The percentage of non-coarse fiber used in the slush overlay process for optimal retention of zinc borate within the hardboard substrate should be at least about 75%, more preferably at about 86% or higher (e.g. coarse fiber at <14%).

The hardboard substrate containing borate produced by the inventive process meets the American Wood Preservers' Association standards of greater than 0.38% BAE for preserved wood products. Additionally, the integration of both zinc borate and an increased level of resin retention can result in a greater board density, higher modulus of rupture, lower water absorption, and lower thickness swell which would result in improved overall decay resistance of the board as well as decreased leachability of the borate from the substrate board. The hardboard should most preferably contain zinc to borate in the ratio of up to approximately 1 zinc to 1 borate. Chemically, this means that the zinc borate chemistry is balanced/neutral and that one zinc is present for every borate ion within the hardboard substrate and that the electrochemical bond between the zinc and borate has not been broken. The significance of this is that a ratio of one zinc to less than one borate indicates that the chemical bond between the zinc and borate has been broken and that a fraction of borate ions are released and thus soluble, and therefore will not be retained within the hardboard. Practically, under leaching conditions where the hardboard is subjected to water, the borate ion is more mobile and leachable when not in a one-to-one ratio of zinc to borate. By using the novel process of integrating zinc borate into the overlay slush process while maintaining specific control over process parameters such as temperature, pH, resin type, and fiber content of the overlay slush process, a zinc to borate ratio of at least one zinc to 0.5 borate, more preferably one zinc to about 0.75 borate, can be achieved with upper limits of about one zinc to about one borate.

Overall, the novel process can produce a wet process hardboard substrate which retains zinc borate at a level of over 1.0% BAE. Because the overlay process relies on vacuum pressure for pulling zinc borate down through the hardboard substrate, there is a gradient within the hardboard substrate of zinc borate from the top surface of the hardboard through to the bottom of the board.

Now referring to FIG. 6, hardboard 60 is a cross-section view of a hardboard containing zinc borate produced by the inventive process. Layer 62 is the upper one-third of the hardboard; the layer in contact with the overlay slush contains zinc borate during the overlay slush processing. Layer 62 contains approximately 1% to about 1.6% by weight of zinc borate in this upper third of hardboard 60. Layer 64, the inner layer, contains approximately 0.5% to about 1.0% of zinc borate in the center third of the hardboard's thickness. As follows, the bottom most layer, layer 66, contains approximately up to about 0.5% by weight of zinc borate, more preferably of from about 0.38% to about 0.5% by weight of zinc borate in this bottom third of hardboard 60.

As illustrated by FIG. 7, another useful feature of this novel process is the beneficial cleansing action of the zinc borate in the process. In constructing the treated hardboard, a press is utilized subsequent to overlaying the hardboard substrate with the overlay slush. When the press used for making the hardboard is clean, steam flows at approximately about 4500 lbs/hour across the press, thus raising the temperature of the process to a desired level. In creating wet-process hardboard, wood, resin and wax from both the overlay slush and paper overlay process accumulate on the press and become carbonized from the high temperatures of the steam. Over time, the carbonization accrues on the press causing the steam flow rate to decease and thus necessitates that the press be manually cleaned or scraped so as to increase steam flow to back to the initial flow rate of about 4500 lbs/hour. Specifically, the carbonization should be removed from the press when the flow rate of the steam is diminished to about 2800 lbs/hour. In a process in which the overlay slush does not contain zinc borate, the press can carbonize steadily over a period of about 72 hours to a steam flow rate of about 2800 lbs/hour, thus requiring the press to be cleaned.

With zinc borate in the overlay slush of the process with an initial steam flow rate of about 4500 lbs/hr, after 72 hours, the flow rate of the steam decreases to about 3900 lbs/hr. When compared to the process without the zinc borate, the zinc borate addition provides for a steam flow rate of over about 1000 lbs/hr greater than the process without zinc borate. Thus, the addition of zinc borate slows the carbonization of the press allowing for a greater duration of time before the press has to be taken offline and scraped clean. With the addition of zinc borate, two different chemical phenomena occur. The higher pH of the overall chemistry of a process containing zinc borate, reduces hydrolysis of resin, wax, and zinc borate so more chemistry stays in the board and does not pyrolyze onto the press as carbon. Second, a portion of the zinc borate during the pressing converts to boric acid and serves to assist in cleansing carbon from the press plates and frame.

Accordingly, by the practice of the present invention, a method for delivering and retaining borate within wet process hardboard is disclosed. Furthermore, a novel wet process hardboard is prepared which exhibits improved resistance to natural environmental stresses such as degradation to wood and/or wood composites caused by water and termite penetration which makes the novel hardboard uniquely effective at applications such as for use in building materials.

The disclosures of all cited patents and publications referred to in this application are incorporated herein by reference.

The above description is intended to enable the person skilled in the art to practice the invention. It is not intended to detail all of the possible variations and modifications that will become apparent to the skilled worker upon reading the description. It is intended, however, that all such modifications and variations be included within the scope of the invention that is defined by the following claims. The claims are intended to cover the indicated elements and steps in any arrangement or sequence that is effective to meet the objectives intended for the invention, unless the context specifically indicates the contrary.

Thus, although there have been described particular embodiments of the present invention of a new and useful Treated Wet Process Hardboard, it is not intended that such references be construed as limitations upon the scope of this invention except as set forth in the following claims.

What is claimed is:

1. A method for producing a treated hardboard comprising:
    a) creating a slush containing a borate, cellulose fiber, and lignin;
    b) adjusting the pH of the slush to decrease the solubility of the borate to form overlay slush;
    c) providing a wet fiber hardboard mat;
    d) adjusting the pH of the wet fiber hardboard mat to create pH-controlled hardboard mat;
    e) depositing the overlay slush on the top of the pH-controlled hardboard mat; and
    f) applying vacuum pressure during step e) to create a treated hardboard.

2. The method of claim 1 wherein the borate of step a) is zinc borate.

3. The method of claim 1 wherein the borate of step a) is selected from the group consisting of sodium borate, calcium borate and combinations thereof.

4. The method of claim 1 wherein the pH of the overlay slush of step b) is of from about 4.0 to about 10.0.

5. The method of claim 4 wherein the pH of the overlay slush of step b) is of from about 7.0 to about 8.0.

6. The method of claim 1 wherein the pH of the pH-controlled hardboard mat of step d) is of from about 2.0 to about 6.0.

7. The method of claim 6 wherein the pH of the pH-controlled hardboard mat of step d) is of from about 4.0 to about 5.0.

8. The method of claim 1 wherein the slush of step a) further comprises a phenol-formaldehyde resin.

9. The method of claim 8 wherein the resin is at most at about 2% dry weight of the slush.

10. The method of claim 1 wherein the fiber is of from about 75% to about 100% non-coarse fiber of the total fiber present.

11. The method of claim 10 wherein the fiber is of at least about 86% non-coarse fiber of the total fiber present.

12. The method of claim 1 wherein the pH-controlled hardboard mat of step e) is at a temperature of from about 43° C. to about 60° C.

13. The method of claim 12 wherein the temperature is of from about 48° C. to about 55° C.

14. The method of claim 1 wherein the overlay slush of step e) is at a temperature of from about 15° C. to about 33° C.

15. The method of claim 14 wherein the temperature is of from about 21° C. to about 24° C.

16. The method of claim 1 further comprising step g) wherein the treated hardboard undergoes a finishing process and creates a dust byproduct.

17. The method of claim 16 wherein the dust byproduct is recycled and used in forming the slush of step a).

18. A method for producing a treated hardboard comprising:
  a) creating a slush containing a borate, resin, fiber, and water;
  b) adjusting the pH of the slush to a range of from about 4.0 to about 10.0 to form overlay slush;
  c) providing a wet fiber hardboard mat;
  d) adjusting the pH of the wet fiber hardboard mat of from about 2.0 to about 6.0 to create a pH-controlled hardboard mat;
  e) depositing the overlay slush with a temperature of from about 21° C. to about 24° C. on the top of the pH-controlled hardboard mat;
  f) applying vacuum pressure during step e) to create a treated hardboard; and
  g) finishing the treated hardboard.

19. The method of claim 18 wherein the pH of the overlay slush of step b) is within a range of from about 7.0 to about 8.0.

20. The method of claim 18 wherein the pH of the pH-controlled wet fiber hardboard mat substrate of step d) is within a range of from about 4.0 to about 5.0.

* * * * *